Sept. 22, 1964 R. G. JELLY Plant Pat. 2,447
ROSE PLANT
Filed Oct. 23, 1963
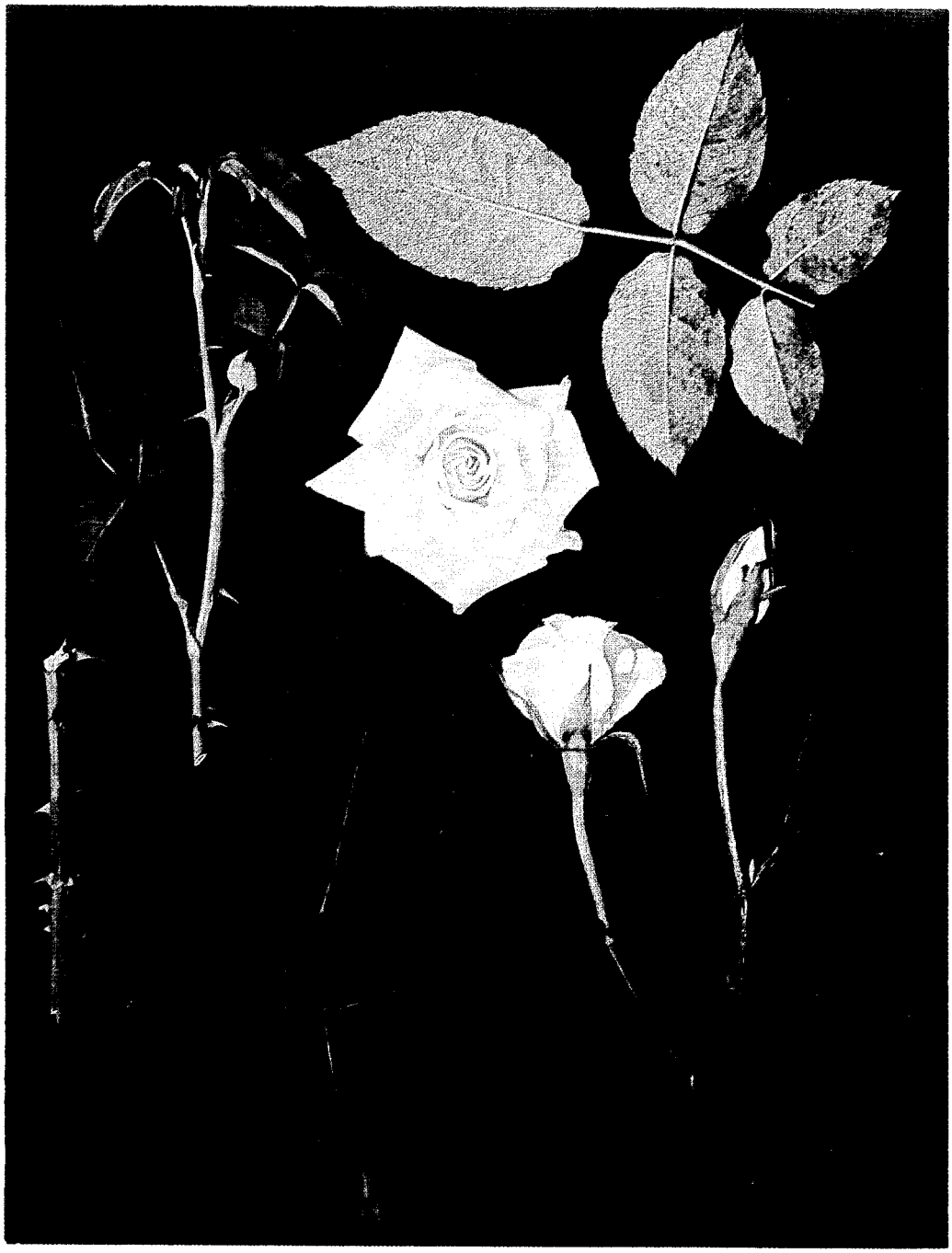
Inventor.
Robert G. Jelly
By: Robb & Robb
Attorneys.

United States Patent Office

Plant Pat. 2,447
Patented Sept. 22, 1964

2,447
ROSE PLANT

Robert G. Jelly, Richmond, Ind., assignor to E. G. Hill Co., Inc., Richmond, Ind., a corporation of Indiana Filed Oct. 23, 1963, Ser. No. 318,444
1 Claim. (Cl. Plt.—23)

The present invention relates to a new and distinct variety of rose plant of the floribunda class, which was originated by me by crossing the variety "Garnette" (unpatented) with an unnamed and unpatented White seedling identified in my breeding records as #2–56W.

The primary objective of this breeding was to produce a new white floribunda rose variety in which there is combined the excellent flower keeping qualities and texture of the seed parent "Garnette." This objective was fully achieved, along with other desirable improvements, as evidenced by the following unique combination of characteristics which are outstanding in the new variety and which distinguish it from its parents, as well as from all other varieties of which I am aware:

(1) A classic form comparable to that of the unnamed pollen parent;

(2) Superior stem length;

(3) Superior bud form;

(4) An excellent and distinctive flower form and texture;

(5) A distinctive and attractive clean-white flower color; and (6) Excellent keeping qualities of the flowers as cut flowers;

In comparison with its seed parent "Garnette," the new variety is superior in a number of respects, including superior bud form and stem length, while maintaining the texture of this parent, and the flowers are white instead of red like the seed parent.

As compared with the unnamed pollen parent, the new variety is a floribunda instead of a hybrid tea like this parent, while maintaining the classic form of this parent.

The variety "Cotton Top" (Plant Patent No. 1,886) is probably the most similar floribunda rose variety grown for commercial cut flower production but the new variety is a great improvement thereover in both flower form and texture.

Asexual reproduction of the new variety by grafting, as performed at Richmond, Indiana, and also by budding, as performed at Livermore, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert S. Wilson's Horticultural Colour Chart (hereinafter abbreviated as (W)), and Nickerson Color Fan (hereinafter abbreviated as (N)), as indicated, except where general color terms of ordinary dictionary significance are obvious:

Type: Seedling; greenhouse; for cut flowers.
Class: Floribunda.
Breeding: Seedling.
*Seed parent.*—"Garnette."
*Pollen parent.*—An unnamed white seedling identified as #2–56W.
Propagation: Holds its distinguishing characteristics through succeeding propagations by both grafting and budding.

*Flower*

Locality where grown and where following observations were made: Richmond, Indiana.
Flowers borne: From 1 to 3 to a stem, but generally disbudded to one to a stem for commercial cut flower production; in irregular clusters; on moderately strong stems of medium length.
Quantity of bloom: Abundant, in greenhouse.
Continuity: Continuous, in greenhouse.
Fragrance: Moderate, in greenhouse. Nature—tea.
Bud:
*Peduncle.*—Medium length; medium diameter; erect; medium strong. Bark—very slightly rough, with few to several prickles of Brilliant Yellow Green, Plate 2.5GY 9/8 (N). Color—varies from Strong Yellow Green, Plate 2.5GY 6/8 (N) to Strong Yellow Green, Plate 5GY 6/8 (N). Thorns—none. Prickles—several to few; color—Brilliant Yellow Green, Plate 2.5GY 9/8 (N). Hairs—none.
*Before calyx breaks.*—Size—medium. Form—long pointed; without a conspicuous neck; with foliaceous appendages on the surface of the bud from ¼ inch to ½ inch long, but not extending beyond the tip of the bud. Color—shaded from Moderate Yellow Green, Plate 5GY 5/6 (N) to Brilliant Yellow Green, Plate 2.5GY 8/9 (N) at base.
*As calyx breaks.*—Color—Uranium Green, Plate 63/3 (W), with venation of Uranium Green, Plate 63/1 (W) at base.
*As first petal opens.*—Size—medium. Form—long pointed. Color: outside—Uranium Green, Plate 63/3 (W), with base and venation of Uranium Green, Plate 63/1 (W); inside—Uranium Green, Plate 63/3 (W), with venation and base of Uranium Green, Plate 63/2 (W).
*Opening.*—Opens up well in greenhouse; is unaffected by cold weather except for a slight tinge of green color in the blooms during prolonged periods of cloudy weather coupled with short days.
Bloom:
*Size (when fully open).*—From medium to small; from 2¼ inches to 3½ inches.
*Petalage.*—Very double; from 38 to 48 petals; arranged regularly.
*Form.*—High-centered at first, but becoming from high-centered to globular; petals being at first tightly rolled inward, but later becoming tightly rolled outward at maturity.
Petals:
*Texture.*—Moderately thin.
*Appearance.*—Inside—satiny. Outside—slightly satiny.
*Shape.*—Outer—from ovate to obovate; fairly flat; some with a slight apex. Intermediate—from ovate to obovate, with apex fairly flat. Inner—from ovate to obovate, with apex from flat to rounded.

This description of a newly opened flower was made from a rose grown in a greenhouse during the month of January at Richmond, Indiana.

*Color.*—Outer petal: outside surface—white, with Brilliant Yellow Green, Plate 2.5GY 8/9 (N) base and lower venation near base; inside surface—white, with base and lower venation Brilliant Yellow Green, Plate 2.5GY 9/8 (N). Intermediate petal: outside surface—white, with Brilliant Greenish Yellow, Plate 7.5Y 9/8 (N) base; inside surface—white, with small area at base of Dresden Yellow, Plate 64/2 (W). Inner petal: outside surface—white, with base of Dresden Yellow, Plate 64/3 (W); inside surface—white, with base of Dresden Yellow, Plate 64/3 (W).

This description was made from a rose that was open for three days in a greenhouse during the month of January at Richmond, Indiana.

*Color.*—Outer petal: outside surface—white, with slight area at base of Sulphur Yellow, Plate 1/3 (W); inside surface—white, with slight area at base of Sulphur Yellow, Plate 1/3 (W). Intermediate petal: outside surface—white, with slight area at base of Dresden Yellow, Plate 64/3 (W); inside surface—white, with slight area at base of Sulphur Yellow, Plate 1/3 (W). Inner petal: outside surface—white, with slight area at base of Sulphur Yellow, Plate 1/3 (W); inside surface—white, with slight area at base of Sulphur Yellow, Plate 1/3 (W).

*General color effect.*—Newly opened flower—white, with Sulphur Yellow, Plate 1/3 (W) cast toward center. 3-days open—white, with slight Sulphur Yellow, Plate 1/3 (W) cast toward center.

*Behavior.*—Petals persist in greenhouse; not affected by weather.

*Flower longevity.*—Cut flowers grown in greenhouse and kept at living room temperatures—7 days in November.

*Plant*

Foliage:

*Leaves.*—Compound of 3–7 leaflets; normal abundance; medium size; from thin to average thickness; dull.

*Leaflets.*—Shape—from oval to slightly cordate. Apex—cuspidate. Base—from obtuse to slightly cordate. Margin—serrate.

*Color.*—Mature: upper surface—Moderate Olive Green, Plate 5GY 4/3 (N), but tending to a darker appearance by Grayish Olive Green venation, Plate 5GY 3/2 (N); under surface—a shade Greener than Lavender Green, Plate 000761/1 (W). Young: upper surface—shaded from Moderate Yellow Green, Plate 7.5GY 5/7 (N) to slightly darker than Moderate Oliver Green, Plate 5GY 4/3 (N); under surface—Sage Green, Plate 000861/1 (W).

*Rachis (the supporting stem of the compound leaf).*—Medium. Upper side—grooved; moderately prickly. Under side—a few thorns to each compound leaflet.

*Stipules.*—Medium length; narrow; with short points turning out at an angle of less than 45°.

Growth (in greenhouse):

*Habit.*—Upright; much-branched.

*Growth.*—Free; vigorous.

*Canes.*—Medium diameter.

*Main stems.*—Color—Spinach Green, Plate 0960/2 (W). Thorns—several; medium length; hooked slightly downward; with narrow base; color—Moderate Brown, Plate 7.5YR 4/5 (N). Prickles—none. Hairs—none.

*Branches.*—Color—Spinach Green, Plate 0960/2 (W). Thorns—several; from long to medium length; from straight to hooked slightly downward; with very short narrow base; color—varies from Moderate Brown, Plate 7.5YR 4/5 (N) to Moderate Brown, Plate 5YR 3/3 (N). Prickles—none. Hairs—none.

*New shoots.*—Color—varies from Spinach Green, Plate 0960 (W) to Scheeles Green, Plate 860/2 (W). Thorns—few; short; hooked slightly downward; with short, narrow base; color—shaded from Naples Yellow, Plate 503 (W) at tip to slightly darker than Brick Red, Plate 016/2 (W) at base. Prickles—none. Hairs—none.

*Reproductive Organs*

Stamens: Medium number; arranged irregularly about pistils; mixed with petaloids.

Filaments: Medium length; many with anthers. Color—Brilliant Greenish Yellow, Plate 7.5Y 9/8 (N).

Anthers: From medium size to small; open at various times. Color—Yellow Ochre, Plate 07/2 (W).

Pollen: Moderate quantity. Color—Yellow Ochre, Plate 07/1 (W).

Pistils: Medium number.

Styles: Uneven; medium length; moderately thin; loosely bunched. Color—Primrose Yellow, Plate 601/1 (W).

Stigma: Color—Sulphur Yellow, Plate 1/2 (W).

Ovaries: Some protruding from calyx.

Hips: From short to medium length; from ovoid to oblong; with a conspicuous neck; pear-shaped; very smooth; walls thick and fleshy. Color—not quite as bright as Strong Orange, Plate 5YR 7/11 (N).

Sepals: Permanent; medium length; spear-shaped; recurved. Color: inside—Moderate Yellow Green, Plate 5GY 5/6 (N) at edge when bloom opens, with center and base Brilliant Yellow Green, Plate 2.5GY 9/8 (N); outside—Moderate Yellow Green, Plate 5GY 5/6 (N) shaded to Brilliant Yellow Green, Plate 2.5GY 9/8 (N) at base.

Seeds: Few; from small to medium size.

I claim:

A new and distinct variety of rose plant of the floribunda class, substantially as herein shown and described, characterized particularly as to novelty by the unique combination of a classic form comparable to that of its pollen parent, superior stem length, superior bud form, an excellent and distinctive flower form and texture, a distinctive and attractive clean-white flower color, and excellent keeping qualities of the flowers as cut flowers, No references cited.